(12) United States Patent
Parrinello et al.

(10) Patent No.: US 10,842,902 B2
(45) Date of Patent: Nov. 24, 2020

(54) TREATED MEMBRANE FOR FRAGRANCE DELIVERY

(71) Applicant: PPG Industries Ohio, Inc., Cleveland, OH (US)

(72) Inventors: Luciano M. Parrinello, Allison Park, PA (US); Qunhui Guo, Murrysville, PA (US)

(73) Assignee: PPG Industries Ohio, Inc., Cleveland, OH (US)

( * ) Notice: Subject to any disclaimer, the term of this patent is extended or adjusted under 35 U.S.C. 154(b) by 0 days.

(21) Appl. No.: 15/809,255

(22) Filed: Nov. 10, 2017

(65) Prior Publication Data

US 2019/0070330 A1 Mar. 7, 2019

Related U.S. Application Data

(60) Provisional application No. 62/553,350, filed on Sep. 1, 2017.

(51) Int. Cl.
*A61L 9/04* (2006.01)
*B01D 69/10* (2006.01)
*A61L 9/12* (2006.01)
*B01D 71/26* (2006.01)
*B01D 67/00* (2006.01)

(52) U.S. Cl.
CPC .............. *A61L 9/042* (2013.01); *A61L 9/044* (2013.01); *A61L 9/12* (2013.01); *B01D 67/0088* (2013.01); *B01D 69/10* (2013.01); *B01D 71/26* (2013.01); *A61L 9/046* (2013.01); *A61L 9/048* (2013.01); *A61L 9/127* (2013.01); *A61L 2209/131* (2013.01); *B01D 2323/04* (2013.01); *B01D 2323/21* (2013.01)

(58) Field of Classification Search
CPC .......... A61L 9/042; A61L 9/044; A61L 9/127; B01D 2323/04; B01D 2323/21
See application file for complete search history.

(56) References Cited

U.S. PATENT DOCUMENTS

| 2,772,322 A | 11/1956 | Witt et al. |
| 2,940,830 A | 6/1960 | Thornhill |
| 3,696,061 A | 10/1972 | Selsor et al. |
| 3,862,030 A | 1/1975 | Goldberg |
| 4,681,750 A | 7/1987 | Johnson et al. |

(Continued)

FOREIGN PATENT DOCUMENTS

| EP | 0836857 A1 * | 4/1998 | .......... A01M 1/2033 |
| RU | 2342954 C2 | 1/2009 | |

(Continued)

*Primary Examiner* — Hai Vo
(74) *Attorney, Agent, or Firm* — The Webb Law Firm (57) ABSTRACT

A treated vapor permeable microporous membrane includes: a microporous membrane having a first side and a second side opposite the first side. The membrane includes a thermoplastic organic polymer having a polyolefin. The membrane defines a network of interconnecting pores communicating substantially throughout the membrane. The treated membrane further includes finely divided, particulate filler distributed throughout the membrane and a first hydrophobic/oleophobic material over at least a portion of the first side. A method of preparing the treated vapor permeable microporous membrane is also disclosed.

22 Claims, 1 Drawing Sheet

(56) References Cited

U.S. PATENT DOCUMENTS

| | | | |
|---|---|---|---|
| 4,937,115 A * | 6/1990 | Leatherman | B32B 5/18 |
| | | | 428/315.5 |
| 5,326,391 A | 7/1994 | Anderson et al. | |
| 6,013,732 A | 1/2000 | Yamana et al. | |
| 6,261,678 B1 | 7/2001 | von Fragstein et al. | |
| 6,387,519 B1 | 5/2002 | Anderson et al. | |
| 7,985,497 B2 | 7/2011 | Takita et al. | |
| 7,988,895 B2 | 8/2011 | Takita et al. | |
| 8,277,661 B2 | 10/2012 | Sah et al. | |
| 8,551,895 B2 | 10/2013 | Yahiaoui et al. | |
| 8,567,693 B2 | 10/2013 | Roreger et al. | |
| 8,932,748 B2 | 1/2015 | Kikuchi et al. | |
| 2002/0054969 A1 * | 5/2002 | Clarke | B32B 5/18 |
| | | | 428/35.2 |
| 2008/0237117 A1 * | 10/2008 | Bansal | B01D 67/0088 |
| | | | 210/490 |
| 2009/0170005 A1 | 7/2009 | Kimishima et al. | |
| 2010/0272914 A1 * | 10/2010 | Chen | B32B 27/12 |
| | | | 427/398.1 |
| 2010/0272941 A1 | 10/2010 | Cherukupalli et al. | |
| 2011/0256364 A1 * | 10/2011 | Boyer | A61L 9/042 |
| | | | 428/212 |
| 2013/0228519 A1 | 9/2013 | Guo et al. | |
| 2013/0228529 A1 | 9/2013 | Guo et al. | |
| 2016/0317974 A1 * | 11/2016 | Hellring | C02F 1/44 |

FOREIGN PATENT DOCUMENTS

| | | |
|---|---|---|
| RU | 2406561 C2 | 12/2010 |
| RU | 2418623 C2 | 5/2011 |
| RU | 2423173 C2 | 7/2011 |
| RU | 2424044 C2 | 7/2011 |
| RU | 2431521 C2 | 10/2011 |
| RU | 2580918 C2 | 4/2016 |
| RU | 2593769 C2 | 8/2016 |
| TW | 201410456 A | 3/2014 |
| WO | 9749552 A1 | 12/1997 |
| WO | 2009065092 A1 | 5/2009 |
| WO | 2015050784 A1 | 4/2015 |
| WO | 2015073161 A1 | 5/2015 |

* cited by examiner

TREATED MEMBRANE FOR FRAGRANCE DELIVERY

CROSS REFERENCE TO RELATED APPLICATIONS

This application claims priority to U.S. Provisional Patent Application Ser. No. 62/553,350, filed Sep. 1, 2017, which is hereby incorporated by reference in its entirety.

FIELD OF THE INVENTION

The present invention relates to treated vapor permeable microporous membranes and methods of preparing treated vapor permeable microporous membranes.

BACKGROUND OF THE INVENTION

Fragrance delivery devices often include vapor permeable microporous membranes for uniform release of a fragrance, such as a fragrance oil, over time. The membrane includes a volatile material contact surface in contact with a fragrant oil in liquid form. Opposite the volatile material contact surface is a vapor release surface for releasing the fragrant oil in vapor form. The fragrance delivery device operates by the volatile liquid vaporizing and passing through the membrane. The vaporized oil is released to the atmosphere on the vapor release surface of the membrane.

A problem posed by known fragrance delivery devices including vapor permeable microporous membranes is preventing "sweating" of the fragrant oil under restricted air flow conditions. Sweating occurs when the volatile fragrant oil collects in liquid form on the vapor release surface of the membrane. This can lead to the fragrance delivery device leaking the fragrant oil onto the area surrounding the fragrance delivery device. For example, sweating can lead to liquid fragrant oil from the fragrance delivery device leaking onto household furniture or onto an interior surface of an automobile.

Another challenge posed by known fragrance delivery devices including vapor permeable microporous membranes is uniform fragrance delivery throughout the lifespan of the fragrance delivery device. If the rate at which the fragrant oil is released is too slow, the fragrance may not be detectable and may not freshen the surrounding air. Conversely, if the rate at which the fragrant oil is released is too fast, the fragrance may be overpowering and the lifespan of the fragrance delivery device may be reduced with the fragrant oil being consumed at a high rate.

Therefore, there is a need in the art for a fragrance delivery device that prevents sweating of liquid oil from the fragrance delivery device. Further, development of a fragrance delivery device that releases a uniform and appropriate amount of fragrance through the lifespan of the fragrance delivery device is also desirable.

SUMMARY OF THE INVENTION

The present invention is directed to a treated vapor permeable microporous membrane including a substantially water-insoluble microporous membrane having a first side and a second side opposite the first side. The membrane includes a thermoplastic organic polymer having a polyolefin. The membrane defines a network of interconnecting pores communicating substantially throughout the membrane. Finely divided, substantially water-insoluble particulate filler is distributed throughout the membrane constituting 10 to 90 weight percent of the membrane, based on the total weight of the membrane and the particulate filler. A first hydrophobic/oleophobic material is located over at least a portion of the first side. The polyolefin includes at least 2 weight percent of the membrane, based on the total weight of the membrane and the particulate filler. The membrane has a mean pore size of up to 0.2 µm The present invention is also directed to a method of preparing a treated vapor permeable microporous membrane. The method includes: providing a substantially water-insoluble microporous membrane having a first side and a second side opposite the first side, the membrane including a thermoplastic organic polymer having a polyolefin, the membrane defining a network of interconnecting pores communicating substantially throughout the membrane, the membrane having finely divided, substantially water-insoluble particulate filler distributed throughout the membrane; and applying a first hydrophobic/oleophobic material over at least a portion of the first side.

DESCRIPTION OF THE INVENTION

For purposes of the following detailed description, it is to be understood that the invention may assume various alternative variations and step sequences, except where expressly specified to the contrary. Moreover, other than in any operating examples, or where otherwise indicated, all numbers expressing, for example, quantities of ingredients used in the specification and claims are to be understood as being modified in all instances by the term "about". Accordingly, unless indicated to the contrary, the numerical parameters set forth in the following specification and attached claims are approximations that may vary depending upon the desired properties to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard variation found in their respective testing measurements.

Also, it should be understood that any numerical range recited herein is intended to include all sub-ranges subsumed therein. For example, a range of "1 to 10" is intended to include all sub-ranges between (and including) the recited minimum value of 1 and the recited maximum value of 10, that is, having a minimum value equal to or greater than 1 and a maximum value of equal to or less than 10.

In this application, the use of the singular includes the plural and plural encompasses singular, unless specifically stated otherwise. In addition, in this application, the use of "or" means "and/or" unless specifically stated otherwise, even though "and/or" may be explicitly used in certain instances. Further, in this application, the use of "a" or "an" means "at least one" unless specifically stated otherwise. For example, "an" oil rating, "a" fluoropolymer, and the like refer to one or more of these items. Also, as used herein, the term "polymer" is meant to refer to prepolymers, oligomers, and both homopolymers and copolymers. The term "resin" is used interchangeably with "polymer."

As used herein, the transitional term "comprising" (and other comparable terms, e.g., "containing" and "including") is "open-ended" and is used in reference to compositions, methods, and respective component(s) thereof that are essential to the invention, yet open to the inclusion of unspecified matter. The term "consisting essentially of" refers to those component(s) required for a given embodiment and permits the presence of component(s) that do not materially affect the properties or functional characteristic(s) of that embodiment. The term "consisting of" refers to compositions and methods that are exclusive of any other component not recited in that description of the embodiment.

Figure 1:
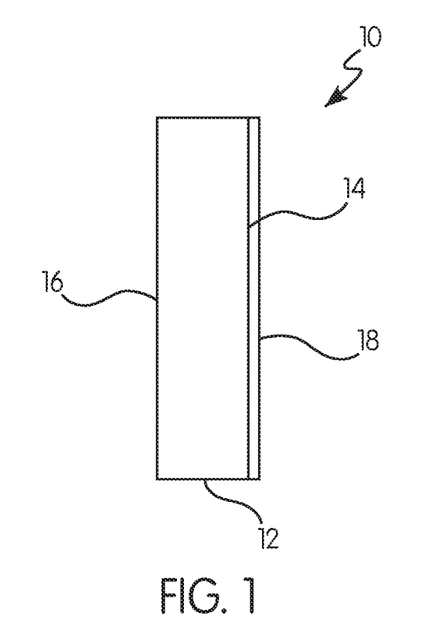
FIG. 1 shows a non-limiting example of a treated vapor permeable microporous membrane according to the present invention.
Figure 2:
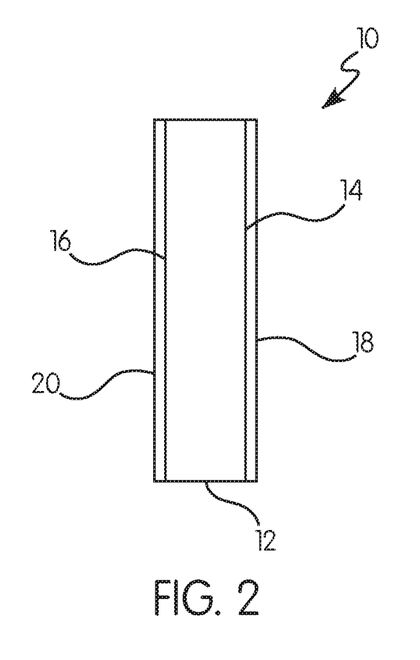
FIG. 2 shows another non-limiting example of a treated vapor permeable microporous membrane according to the present invention.
Figure 3:
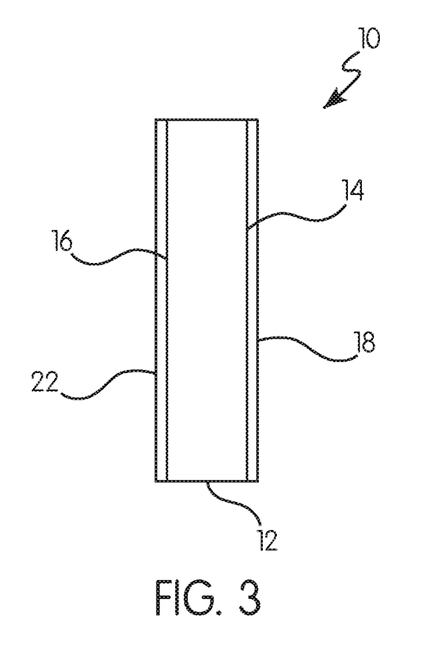
FIG. 3 shows another non-limiting example of a treated vapor permeable microporous membrane according to the present invention.

Referring to FIGS. 1-3, a treated vapor permeable microporous membrane 10 (hereinafter "treated membrane") includes a microporous membrane 12 having a first side 14 and a second side 16 opposite the first side 14. The membrane includes a thermoplastic organic polymer including a polyolefin. The membrane defines a network of interconnecting pores communicating substantially throughout the membrane 12. Finely divided, particulate filler may be distributed throughout the membrane 12. A first hydrophobic/oleophobic material 18 may cover at least a portion of the first side 14.

Microporous Membrane

The membrane 12 may include a thermoplastic organic polymer. In some examples, the thermoplastic organic polymer may be a substantially water-insoluble thermoplastic organic polymer. Substantially water-insoluble means having <50 mg/L solubility in pure water at 25° C.

The types of polymers suitable for use in the membrane 12 are numerous. In general, any substantially water-insoluble thermoplastic organic polymer which can be extruded, calendered, pressed, or rolled into film, sheet, strip, or web may be used. The polymer may be a single polymer or it may be a mixture of polymers. The polymers may be homopolymers, copolymers, random copolymers, block copolymers, graft copolymers, atactic polymers, isotactic polymers, syndiotactic polymers, linear polymers, or branched polymers. When mixtures of polymers are used, the mixture may be homogeneous or it may comprise two or more polymeric phases.

An example of suitable substantially water-insoluble thermoplastic organic polymers includes thermoplastic polyolefins. The polyolefins may comprise at least 2 weight percent, such as at least 5 weight percent, at least 10 weight percent, at least least 15 weight percent, at least 25 weight percent, at least 35 weight percent, at least 45 weight percent, at least 55 weight percent, at least 65 weight percent, at least 75 weight percent, or at least 85 weight percent of the membrane 12, based on the total weight of the membrane 12 including particulate filler. The polyolefins may comprise up to 95 weight percent, such as up to 85 weight percent, up to 75 weight percent, up to 65 weight percent, up to 55 weight percent, up to 45 weight percent, up to 35 weight percent, up to 25 weight percent, or up to 15 weight percent of the membrane 12, based on the total weight of the membrane 12 including particulate filler. The polyolefin may comprise 2 to 95 weight percent of the membrane 12, based on the total weight of the membrane 12 including particulate filler. Other examples of classes of suitable substantially water-insoluble organic polymers may include poly(halo-substituted olefins), polyesters, polyamides, polyurethanes, polyureas, poly(vinyl halides), poly(vinylidene halides), polystyrenes, poly(vinyl esters), polycarbonates, polyethers, polysulfides, polyimides, polysilanes, polysiloxanes, polycaprolactones, polyacrylates, and polymethacrylates. Contemplated hybrid classes, from which the substantially water-insoluble thermoplastic organic polymers may be selected include, for example, thermoplastic poly(urethane-ureas), poly(ester-amides), poly(silane-siloxanes), and poly(ether-esters). Further examples of suitable substantially water-insoluble thermoplastic organic polymers may include thermoplastic high density polyethylene, low density polyethylene, ultrahigh molecular weight polyethylene, polypropylene (atactic, isotactic, or syndiotactic), poly(vinyl chloride), polytetrafluoroethylene, copolymers of ethylene and acrylic acid, copolymers of ethylene and methacrylic acid, poly(vinylidene chloride), copolymers of vinylidene chloride and vinyl acetate, copolymers of vinylidene chloride and vinyl chloride, copolymers of ethylene and propylene, copolymers of ethylene and butene, poly(vinyl acetate), polystyrene, poly(omega-aminoundecanoic acid), poly(hexamethylene adipamide), poly(epsilon-caprolactam), and poly(methyl methacrylate). The recitation of these classes and example of substantially water-insoluble thermoplastic organic polymers is not exhaustive, and are provided only for purposes of illustration.

Substantially water-insoluble thermoplastic organic polymers may in particular include, for example, poly(vinyl chloride), copolymers of vinyl chloride, or mixtures thereof. In an embodiment, the water-insoluble thermoplastic organic polymer includes an ultrahigh molecular weight polyolefin selected from: ultrahigh molecular weight polyolefin, e.g., essentially linear ultrahigh molecular weight polyolefin) having an intrinsic viscosity of at least 10 deciliters/gram; or ultrahigh molecular weight polypropylene, e.g., essentially linear ultrahigh molecular weight polypropylene) having an intrinsic viscosity of at least 6 deciliters/gram; or mixtures thereof. In a particular embodiment, the water-insoluble thermoplastic organic polymer includes ultrahigh molecular weight polyethylene, e.g., linear ultrahigh molecular weight polyethylene, having an intrinsic viscosity of at least 18 deciliters/gram.

Ultrahigh molecular weight polyethylene (UHMWPE) is not a thermoset polymer having an infinite molecular weight, but is technically classified as a thermoplastic. However, because the molecules are substantially very long chains, UHMWPE softens when heated but does not flow as a molten liquid in a normal thermoplastic manner. The very long chains and the peculiar properties they provide to UHMWPE may contribute in large measure to the desirable properties of the membrane 12 made using this polymer.

As indicated earlier, the intrinsic viscosity of the UHMWPE is at least about 10 deciliters/gram. Usually the intrinsic viscosity is at least about 14 deciliters/gram. Often the intrinsic viscosity is at least about 18 deciliters/gram. In many cases the intrinsic viscosity is at least about 19 deciliters/gram. Although there is no particular restriction on the upper limit of the intrinsic viscosity, the intrinsic viscosity is frequently in the range of from about 10 to about 39 deciliters/gram, e.g., in the range of from about 14 to about 39 deciliters/gram. In some cases the intrinsic viscosity of the UHMWPE is in the range of from about 18 to about 39 deciliters/gram, or from about 18 to about 32 deciliters/gram.

The nominal molecular weight of UHMWPE is empirically related to the intrinsic viscosity of the polymer according to the equation:

$$M(\text{UHMWPE})=5.3\times10^4[\eta]^{1.37}$$

where M(UHMWPE) is the nominal molecular weight and [η] is the intrinsic viscosity of the UHMW polyethylene expressed in deciliters/gram.

As used herein, intrinsic viscosity is determined by extrapolating to zero concentration the reduced viscosities or the inherent viscosities of several dilute solutions of the UHMWPE where the solvent is freshly distilled decahydronaphthalene to which 0.2 percent by weight, 3,5-di-tert-butyl-4-hydroxyhydrocinnamic acid, neopentanetetrayl ester [CAS Registry No. 6683-19-8] has been added. The reduced viscosities or the inherent viscosities of the UHMWPE are ascertained from relative viscosities obtained at 135° C. using an Ubbelohde No. 1 viscometer in accordance with the general procedures of ASTM D 4020-81, except that several dilute solutions of differing concentration are employed. ASTM D 4020-81 is, in its entirety, incorporated herein by reference.

In one particular example, the matrix comprises a mixture of substantially linear ultrahigh molecular weight polyethylene having an intrinsic viscosity of at least 10 deciliters/gram, and lower molecular weight polyethylene (LMWPE) having an ASTM D 1238-86 Condition E melt index of less than 50 grams/10 minutes and an ASTM D 1238-86 Condition F melt index of at least 0.1 gram/10 minutes. The nominal molecular weight of LMWPE is lower than that of the UHMWPE. LMWPE is thermoplastic and many different types are known. One method of classification is by density, expressed in grams/cubic centimeter and rounded to the nearest thousandth, in accordance with ASTM D 1248-84 (re-approved 1989), as summarized as follows:

TABLE 1

| Type | Abbreviation | Density (g/cm³) |
| --- | --- | --- |
| Low Density Polyethylene | LDPE | 0.910-0.925 |
| Medium Density Polyethylene | MDPE | 0.926-0.940 |
| High Density Polyethylene | HDPE | 0.941-0.965 |

Any or all of these polyethylenes may be used as the LMWPE in the present invention. For some applications, HDPE, may be used because it ordinarily tends to be more linear than MDPE or LDPE. ASTM D 1248-84 (Reapproved 1989) is, in its entirety, incorporated herein by reference.

Processes for making the various LMWPE's are well known and well documented. They include the high pressure process, the Phillips Petroleum Company process, the Standard Oil Company (Indiana) process, and the Ziegler process.

The ASTM D 1238-86 Condition E (that is, 190° C. and 2.16 kilogram load) melt index of the LMWPE is less than about 50 grams/10 minutes. Often the Condition E melt index is less than about 25 grams/10 minutes. Typically, the Condition E melt index is less than about 15 grams/10 minutes.

The ASTM D 1238-86 Condition F (that is, 190° C. and 21.6 kilogram load) melt index of the LMWPE is at least 0.1 gram/10 minutes. In many cases the Condition F melt index is at least about 0.5 gram/10 minutes. Typically, the Condition F melt index is at least about 1.0 gram/10 minutes. ASTM D 1238-86 is, in its entirety, incorporated herein by reference.

Sufficient UHMWPE and LMWPE should be present in the matrix to provide their properties to the membrane 12. Other thermoplastic organic polymers may also be present in the matrix so long as their presence does not materially affect the properties of the membrane 12 in an adverse manner One or more other thermoplastic polymers may be present in the matrix. The amount of the other thermoplastic polymer which may be present depends upon the nature of such polymer. Examples of thermoplastic organic polymers which may optionally be present include, but are not limited to, poly(tetrafluoroethylene), polypropylene, copolymers of ethylene and propylene, copolymers of ethylene and acrylic acid, and copolymers of ethylene and methacrylic acid. If desired, all or a portion of the carboxyl groups of carboxyl-containing copolymers may be neutralized with sodium, zinc, or the like.

In some examples the UHMWPE and the LMWPE together constitute at least about 65 percent by weight of the polymer of the matrix. In some examples, the UHMWPE and the LMWPE together constitute at least about 85 percent by weight of the polymer of the matrix. In some examples, the other thermoplastic organic polymers are substantially absent so that the UHMWPE and the LMWPE together constitute substantially 100 percent by weight of the polymer of the matrix. In some examples, the UHMWPE constitutes substantially all of the polymer of the matrix (e.g., LMWPE is not included in the formulation).

The UHMWPE may constitute at least one percent by weight of the polymer of the matrix. Where the UHMWPE and the LMWPE together constitute 100 percent by weight of the polymer of the matrix of the membrane 12, the UHMWPE may constitute greater than or equal to 40 percent by weight of the polymer of the matrix, such as greater than or equal to 45 percent by weight, or greater than or equal to 48 percent by weight, or greater than or equal to 50 percent by weight, or greater than or equal to 55 percent by weight of the polymer of the matrix. Also, the UHMWPE may constitute less than or equal to 99 percent by weight of the polymer of the matrix, such as less than or equal to 80 percent by weight, or less than or equal to 70 percent by weight, or less than or equal to 65 percent by weight, or less than or equal to 60 percent by weight of the polymer of the matrix. The level of UHMWPE comprising the polymer of the matrix may range between any of these values inclusive of the recited values.

Likewise, where the UHMWPE and the LMWPE together constitute 100 percent by weight of the polymer of the matrix of the membrane 12, the LMWPE may constitute greater than or equal to 1 percent by weight of the polymer of the matrix, such as greater than or equal to 5 percent by weight, or greater than or equal to 10 percent by weight, or greater than or equal to 15 percent by weight, or greater than or equal to 20 percent by weight, or greater than or equal to 25 percent by weight, or greater than or equal to 30 percent by weight, or greater than or equal to 35 percent by weight, or greater than or equal to 40 percent by weight, or greater than or equal to 45 percent by weight, or greater than or equal to 50 percent by weight, or greater than or equal to 55 percent by weight of the polymer of the matrix. Also, the LMWPE may constitute less than or equal to 70 percent by weight of the polymer of the matrix, such as less than or equal to 65 percent by weight, or less than or equal to 60 percent by weight, or less than or equal to 55 percent by weight, or less than or equal to 50 percent by weight, or less than or equal to 45 percent by weight of the polymer of the matrix. The level of the LMWPE may range between any of these values inclusive of the recited values.

It should be noted that for any of the previously described membranes 12 of the present invention, the LMWPE may comprise high density polyethylene.

The membrane 12 may also include finely divided, particulate filler distributed throughout, as later described. The membrane 12 may also include minor amounts of other materials. Minor amounts may be less than or equal to 10 percent by weight, based on total weight of the membrane 12, particulate filler and other materials. The other materials used in processing, may be lubricants, processing plasticizers, organic extraction liquids, water, and the like. Further other materials introduced for particular purposes, such as thermal, ultraviolet and dimensional stability, may optionally be present in the membrane 12 in small amounts, e.g., less than or equal to 15 percent by weight, based on total weight of the membrane 12, particulate filler, and other materials. Examples of such further materials include, but are not limited to, antioxidants, ultraviolet light absorbers, reinforcing fibers such as chopped glass fiber strand, and the like. The balance of the membrane 12, exclusive of filler and any coating, printing ink, or impregnant applied for one or more special purposes is essentially the thermoplastic organic polymer.

Finely Divided, Particulate Filler

As previously mentioned, the membrane 12 may include finely divided, particulate filler distributed through the membrane 12. In one example, the particulate filler includes siliceous particles having particulate silica. The particulate filler may include an organic particulate material and/or an inorganic particulate material. The particulate filler may or may not be colored. For example, the particulate filler material may be a white or off-white particulate filler material, such as siliceous or clay particulate material.

The particulate filler may be substantially water-insoluble filler particles. Substantially water-insoluble means having <50 mg/L solubility in pure water at 25° C.

The finely divided substantially water-insoluble filler particles may constitute from 10 to 90 percent by weight of the membrane 12, the filler particles, and other materials (excluding coating applied to the membrane 12). For example, such filler particles may constitute from 20 percent to 90 percent by weight of the membrane 12, the filler particles, and other materials (excluding coating applied to the membrane 12), such as from 30 percent to 70 percent, or such as from 40 percent to 60 percent.

The finely divided, particulate filler may be in the form of ultimate particles, aggregates of ultimate particles, or a combination of both. At least about 90 percent by weight of the particulate filler used in preparing the membrane 12 may have gross particle sizes in the range of from 0.5 to about 200 micrometers, such as from 1 to 100 micrometers, as determined by the use of a laser diffraction particle size instrument, LS230 from Beckman Coulton, which is capable of measuring particle diameters as small as 0.04 micrometers. At least 90 percent by weight of the particulate filler may have a gross particle sizes in the range of from 5 to 40, e.g., 10 to 30 micrometers. The sizes of the particulate filler agglomerates may be reduced during processing of the ingredients used to prepare the membrane 12. Accordingly, the distribution of gross particle sizes in the membrane 12 may be smaller than in the raw filler itself.

Non-limiting examples of suitable organic and inorganic particulate filler that may be used in the membrane 12 of the present invention may include those described in U.S. Pat. No. 6,387,519 B1 at column 9, line 4 to column 13, line 62, the cited portions of which are incorporated herein by reference.

In a particular embodiment of the present invention, the particulate filler material includes siliceous materials. Non-limiting examples of siliceous fillers that may be used to prepare the microporous material include silica, mica, montmorillonite, kaolinite, nanoclays such as cloisite, which is available from Southern Clay Products (Gonzales, Tex.), talc, diatomaceous earth, vermiculite, natural and synthetic zeolites, calcium silicate, aluminum silicate, sodium aluminum silicate, aluminum polysilicate, alumina silica gels and glass particles. In addition to the siliceous fillers, other finely divided particulate substantially water-insoluble fillers optionally may also be employed. Non-limiting examples of such optional particulate fillers include carbon black, charcoal, graphite, titanium oxide, iron oxide, copper oxide, zinc oxide, antimony oxide, zirconia, magnesia, alumina, molybdenum disulfide, zinc sulfide, barium sulfate, strontium sulfate, calcium carbonate, and magnesium carbonate. Some of such optional fillers are color-producing fillers and, depending on the amount used, may add a hue or color to the microporous material. In a non-limiting embodiment, the siliceous filler may include silica and any of the aforementioned clays. Non-limiting examples of silicas include precipitated silica, silica gel, fumed silica, and combinations thereof.

Silica gel is generally produced commercially by acidifying an aqueous solution of a soluble metal silicate, e.g., sodium silicate, at low pH with acid. The acid employed is generally a strong mineral acid such as sulfuric acid or hydrochloric acid, although carbon dioxide can be used. Inasmuch as there is essentially no difference in density between the gel phase and the surrounding liquid phase while the viscosity is low, the gel phase does not settle out, that is to say, it does not precipitate. Consequently, silica gel may be described as a non-precipitated, coherent, rigid, three-dimensional network of contiguous particles of colloidal amorphous silica. The state of subdivision ranges from large, solid masses to submicroscopic particles, and the degree of hydration from almost anhydrous silica to soft gelatinous masses containing on the order of 100 parts of water per part of silica by weight.

Precipitated silica generally is produced commercially by combining an aqueous solution of a soluble metal silicate, ordinarily alkali metal silicate such as sodium silicate, and an acid so that colloidal particles of silica will grow in a weakly alkaline solution and be coagulated by the alkali metal ions of the resulting soluble alkali metal salt. Various acids may be used, including but not limited to mineral acids. Non-limiting examples of acids that may be used include hydrochloric acid and sulfuric acid, but carbon dioxide can also be used to produce precipitated silica. In the absence of a coagulant, silica is not precipitated from solution at any pH. In a non-limiting embodiment, the coagulant used to effect precipitation of silica may be the soluble alkali metal salt produced during formation of the colloidal silica particles, or it may be an added electrolyte, such as a soluble inorganic or organic salt, or it may be a combination of both.

Many different precipitated silicas can be employed as the siliceous filler used to prepare the microporous material. Precipitated silicas are well-known commercial materials, and processes for producing them are described in detail in many United States patents, including U.S. Pat. Nos. 2,940,830 and 4,681,750. The average ultimate particle size (irrespective of whether or not the ultimate particles are agglomerated) of precipitated silica used to prepare the microporous material is generally less than 0.1 micrometer, e.g., less than 0.05 micrometer or less than 0.03 micrometer, as determined by transmission electron microscopy. Precipitated silicas are available in many grades and forms from PPG Industries, Inc. (Pittsburgh, Pa.). These silicas are sold under the Hi-Sil trademark.

For purposes of the present invention, the finely divided particulate siliceous filler can make up at least 50 percent by weight, e.g., at least 65 or at least 75 percent by weight, or at least 90 percent by weight of the particulate filler material. The siliceous filler may make up from 50 to 90 percent by weight, e.g., from 60 to 80 percent by weight, of the particulate filler, or the siliceous filler may make up substantially all (over 90 percent by weight) of the particulate filler.

The particulate filler, e.g., the siliceous filler, typically has a high surface area, which allows the filler to carry much of the processing plasticizer composition used to produce the microporous material of the present invention. High surface area fillers are materials of very small particle size, materials that have a high degree of porosity, or materials that exhibit both of such properties. The surface area of the particulate filler, e.g., the siliceous filler particles, can range from 20 to 1000 square meters per gram, e.g., from 25 to 400 square meters per gram, or from 40 to 200 square meters per gram, as determined by the Brunauer, Emmett, Teller (BET) method according to ASTM D 1993-91. The BET surface area is determined by fitting five relative pressure points from a nitrogen sorption isotherm measurement made using a Micromeritics TriStar 3000™ instrument. A FlowPrep-060™ station can be used to provide heat and continuous gas flow during sample preparation. Prior to nitrogen sorption, silica samples are dried by heating to 160° C. in flowing nitrogen (PS) for 1 hour. The surface area of any non-siliceous filler particles used may also be within one of these ranges. The filler particles may be substantially water-insoluble and may also be substantially insoluble in any organic processing liquid used to prepare the microporous material. Substantially water-insoluble means having <50 mg/L solubility in pure water at 25° C. Substantially insoluble in an organic processing liquid means having <50 mg/L solubility in the organic processing liquid. This may facilitate retention of the particulate filler within the microporous material.

The membrane 12 may also include a network of interconnecting pores, which communicate substantially throughout the membrane 12. On a coating-free, printing ink free and impregnant-free basis, pores typically constitute from 35 to 95 percent by volume, based on the total volume of the membrane 12, when made by the processes as further described herein. The pores may constitute from 60 to 75 percent by volume of the membrane 12, based on the total volume of the microporous material. As used herein, the porosity (also known as void volume) of the membrane 12, expressed as percent by volume, is determined according to the following equation:

$$\text{Porosity}=100[1-d_1/d_2]$$

where, $d_1$ is the density of the sample, which is determined from the sample weight and the sample volume as ascertained from measurements of the sample dimensions; and $d_2$ is the density of the solid portion of the sample, which is determined from the sample weight and the volume of the solid portion of the sample. The volume of the solid portion of the microporous material is determined using a Quantachrome stereopycnometer (Quantachrome Instruments (Boynton Beach, Fla.)) in accordance with the operating manual accompanying the instrument.

The volume average diameter of the pores of the membrane 12 is determined by mercury porosimetry using an Autoscan mercury porosimeter (Quantachrome Instruments (Boynton Beach, Fla.)) in accordance with the operating manual accompanying the instrument. The volume average pore radius for a single scan is automatically determined by the porosimeter. In operating the porosimeter, a scan is made in the high pressure range (from 138 kilopascals absolute to 227 megapascals absolute). If 2 percent or less of the total intruded volume occurs at the low end (from 138 to 250 kilopascals absolute) of the high pressure range, the volume average pore diameter is taken as twice the volume average pore radius determined by the porosimeter. Otherwise, an additional scan is made in the low pressure range (from 7 to 165 kilopascals absolute) and the volume average pore diameter is calculated according to the equation:

$$d=2[v_1 r_1/w_1 + v_2 r_2/w_2]/[v_1/w_1 + v_2/w_2]$$

where, d is the volume average pore diameter; $v_1$ is the total volume of mercury intruded in the high pressure range; $v_2$ is the total volume of mercury intruded in the low pressure range; $r_1$ is the volume average pore radius determined from the high pressure scan; $r_2$ is the volume average pore radius determined from the low pressure scan; $w_3$ is the weight of the sample subjected to the high pressure scan; and $w_2$ is the weight of the sample subjected to the low pressure scan.

Generally on a coating-free, printing ink-free and impregnant-free basis, the volume average diameter of the pores (mean pore size) of the membrane 12 may be up to 0.5 micrometers, such as up to 0.3 micrometers, or up to 0.2 micrometers. The average diameter of the pores may be at least 0.02 micrometers, such as at least 0.04 micrometers, or at least 0.05 micrometers. The volume average diameter of the pores, on this basis, may range between any of these values, inclusive of the recited values. For example, the volume average diameter of the pores of the membrane 12 may range from 0.02 to 0.15 micrometers, or from 0.02 to 0.1 micrometers, or from 0.02 to 0.075 micrometers, in each case inclusive of the recited values.

In the course of determining the volume average pore diameter by means of the above described procedure, the maximum pore radius detected may also be determined. This is taken from the low pressure range scan, if run; otherwise it is taken from the high pressure range scan. The maximum pore diameter of the microporous material is typically twice the maximum pore radius.

Coating, printing and impregnation processes may result in filling at least some of the pores of the membrane 12. In addition, such processes may also irreversibly compress the membrane 12. Accordingly, the parameters with respect to porosity, volume average diameter of the pores, and maximum pore diameter are determined for the membrane 12 prior to application of one or more of these processes.

The membrane 12, including the finely divided, particulate filler and/or other materials (excluding coating applied to the membrane 12) may have a density between 0.4 g/cm³ and 1.0 g/cm³. The density can range between any of the above-stated values, inclusive of the recited values. As used herein and in the claims, the density of the membrane 12 is determined by measuring the weight and volume of a sample of the microporous material.

The porosity of the membrane 12 may be measured in terms of the rate of air flow through a sample, herein measured and reported as Gurley porosity. The Gurley porosity of the membrane 12, including the finely divided, particulate filler and/or other materials (excluding coating applied to the membrane 12) may be greater than 15 seconds, such as greater than 100 seconds, greater than 200 seconds, greater than 300 seconds, greater than 400 seconds, or greater than 500 seconds. Gurley porosity is determined using a Gurley densometer, model 4340, manufactured by GPI Gurley Precision Instruments of (Troy, N.Y.) The Gurley porosity reported was a measure of the rate of air flow through a sample or it's resistance to an air flow through the sample. The unit of measure is a "Gurley second" and represents the time in seconds to pass 100 cc of air through a 1 inch square ($6.4 \times 10^{-4}$ $m^2$) area using a pressure differential of 4.88 inches of water ($12.2 \times 10^2$ Pa). Lower values equate to less air flow resistance (more air is allowed to pass freely). The measurements were completed using the procedure listed in the manual, *MODEL 4340 Automatic Densometer and Smoothness Tester Instruction Manual*. TAPPI method T 460 om-06-Air Resistance of Paper may also be referenced for the basic principles of the measurement.

Producing the Microporous Membrane

Numerous art-recognized processes may be used to produce the membrane 12. For example, the membrane 12 may be prepared by mixing together filler particles, thermoplastic organic polymer powder, processing plasticizer and minor amounts of lubricant and antioxidant, until a substantially uniform mixture is obtained. The weight ratio of particulate filler to polymer powder employed in forming the mixture may be essentially the same as that of the membrane 12 to be produced. The mixture, together with additional processing plasticizer, may be introduced into the heated barrel of a screw extruder. Attached to the terminal end of the extruder may be a sheeting die. A continuous sheet formed by the die may be forwarded without drawing to a pair of heated calender rolls acting cooperatively to form a continuous sheet of lesser thickness than the continuous sheet exiting from the die. The level of processing plasticizer present in the continuous sheet at this point in the process may vary and may affect the density of the membrane. For example, the level of processing plasticizer present in the continuous sheet, prior to extraction as described herein below, may be greater than or equal to 30 percent by weight of the continuous sheet, such as greater than or equal to 40 percent by weight, or greater than or equal to 45 percent prior to extraction. Also, the amount of processing plasticizer present in the continuous sheet prior to extraction may be less than or equal to 70 percent by weight of the continuous sheet, such as less than or equal to 65 percent, or less than or equal to 60 percent, or less than or equal to 57 percent prior to extraction. The level of processing plasticizer present in the continuous sheet at this point in the process, prior to extraction, may range between any of these values inclusive of the recited values. In one embodiment the amount of processing plasticizer may vary from 57 to 62 weight percent, and in another embodiment be less than 57 weight percent.

The continuous sheet from the calender may then passed to a first extraction zone where the processing plasticizer is substantially removed by extraction with an organic liquid, which is a good solvent for the processing plasticizer, a poor solvent for the organic polymer, and more volatile than the processing plasticizer. Both the processing plasticizer and the organic extraction liquid may be substantially immiscible with water. The continuous sheet may then pass to a second extraction zone where residual organic extraction liquid is substantially removed by steam and/or water. The continuous sheet may then pass through a forced air dryer for substantial removal of residual water and remaining residual organic extraction liquid. From the dryer the continuous sheet, which is the membrane 12, may be passed to a take-up roll.

The processing plasticizer may be a liquid at room temperature and may be a processing oil such as paraffinic oil, naphthenic oil, or aromatic oil. Suitable processing oils include those meeting the requirements of ASTM D 2226-82. Types 103 and 104. Processing oils having a pour point of less than 220° C. according to ASTM D 97-66 (re-approved 1978) may be used to produce the membrane 12. Processing plasticizers useful in preparing the membrane 12 are discussed in further detail in U.S. Pat. No. 5,326,391 at column 10, lines 26 through 50, which disclosure is incorporated herein by reference.

The processing plasticizer composition used to prepare the membrane 12 may have little solvating effect on the polyolefin of the membrane 12 at 60° C., and only a moderate solvating effect at elevated temperatures on the order of 100° C. The processing plasticizer composition may be a liquid at room temperature. Non-limiting examples of processing oils that may be used may include SHELLFLEX® 412 oil, SHELLFLEX® 371 oil (Shell Oil Co. (Houston, Tex.)), which are solvent refined and hydrotreated oils derived from naphthenic crude oils, ARCOprimeX® 400 oil (Atlantic Richfield Co. (La Palma, Calif.)) and KAYDOL® oil (Witco Corp. (Greenwich, Conn.)), which are white mineral oils. Other non-limiting examples of processing plasticizers may include phthalate ester plasticizers, such as dibutyl phthalate, bis(2-ethylhexyl) phthalate, diisodecyl phthalate, dicyclohexyl phthalate, butyl benzyl phthalate, and ditridecyl phthalate. Mixtures of any of the foregoing processing plasticizers may be used to prepare membrane 12.

There are many organic extraction liquids that may be used to prepare the membrane 12. Examples of suitable organic extraction liquids include those described in U.S. Pat. No. 5,326,391 at column 10, lines 51 through 57, which disclosure is incorporated herein by reference.

The extraction fluid composition may include halogenated hydrocarbons, such as chlorinated hydrocarbons and/or fluorinated hydrocarbons. In particular, the extraction fluid composition may include halogenated hydrocarbon(s) and have a calculated solubility parameter coulomb term ($\delta clb$) ranging from 4 to 9 $(Jcm^3)^{1/2}$. Non-limiting examples of halogenated hydrocarbon(s) suitable as the extraction fluid composition for use in producing the membrane 12 may include one or more azeotropes of halogenated hydrocarbons selected from trans-1,2-dichloroethylene, 1,1,1,2,2, 3,4,5,5,5-decafluoropentane, and/or 1,1,1,3,3-pentafluorobutane. Such materials are available commercially as VERTREL MCA (a binary azeotrope of 1,1,1,2,2,3,4,5,5,5-dihydrodecafluoropentane and trans-1,2-dichloroethylene: 62%/38%), and VERTREL CCA (a ternary azeotrope of 1,1,1,2,2,3,4,5,5,5-dihydrodecafluorpentane, 1,1,1,3,3-pentafluorbutane, and trans-1,2-dichloroethylene: 33%/28%/39%), both available from MicroCare Corporation (New Britain, Conn.).

The residual processing plasticizer content of the membrane 12 may be less than 10 percent by weight, based on the total weight of the membrane 12, and this amount may be further reduced by additional extractions using the same or a different organic extraction liquid. The residual processing plasticizer content may be less than 5 percent by weight, based on the total weight of the membrane 12, and this amount may be further reduced by additional extractions.

The membrane 12 may also be produced according to the general principles and procedures of U.S. Pat. Nos. 2,772, 322; 3,696,061; and/or 3,862,030. These principles and procedures are particularly applicable where the polymer of the matrix is or is predominately poly(vinyl chloride) or a copolymer containing a large proportion of polymerized vinyl chloride.

Membranes 12 produced by the above-described processes optionally may be stretched. Stretching of the membrane 12 may result in both an increase in the void volume of the material, and the formation of regions of increased or enhanced molecular orientation. As is known in the art, many of the physical properties of molecularly oriented thermoplastic organic polymer, including tensile strength, tensile modulus, Young's modulus, and others, differ, e.g., considerably, from those of the corresponding thermoplastic organic polymer having little or no molecular orientation. Stretching may be accomplished after substantial removal of the processing plasticizer as described above.

Various types of stretching apparatus and processes are well known to those of ordinary skill in the art, and may be used to accomplish stretching of the membrane 12. Stretching of the membrane 12 is described in further detail in U.S. Pat. No. 5,326,391 at column 11, line 45 through column 13, line 13, which disclosure is incorporated herein by reference.

Treated Microporous Membrane

Subsequent materials may be applied to the membrane 12 to form the treated membrane 10. In some examples, only the first side 14 of the membrane 12 receives the materials. In some examples, only the second side 16 of the membrane 12 receives the materials. In some examples, both the first side 14 and the second side 16 of the membrane 12 receive the materials. A hydrophobic/oleophobic material(s), a hydrophilic coating layer(s), or some combination thereof may be applied to the membrane 12.

A. First Hydrophobic/Oleophobic Material

Referring to FIGS. 1-3, the first hydrophobic/oleophobic material 18 may be applied to the membrane 12. The first hydrophobic/oleophobic material 18 may be applied to the first side 14 of the membrane 12 (as in FIGS. 1-3) and/or the second side 16 of the membrane 12.

The first hydrophobic/oleophobic material 18 may be hydrophobic. Hydrophobic means that the side (such as the first side 14 or the second side 16) of the membrane 12 over which the first hydrophobic/oleophobic material 18 is applied demonstrates a water contact angle of at least 90° using the Kruss Drop Shape Analysis. The side of the membrane 12 over which the first hydrophobic/oleophobic material 18 is applied may demonstrate a water contact angle of at least 105°, such as at least 110°, at least 115°, at least 120°, at least 125°, at least 130°, at least 135°, at least 140°, or at least 150°.

The first hydrophobic/oleophobic material 18 may be oleophobic. Oleophobic means that the side of the membrane 12 over which the first hydrophobic/oleophobic material 18 is applied demonstrates an oil rating of at least 6, such as at least 7 or at least 8, based on AATCC test method 118-2007.

The first hydrophobic/oleophobic material 18 may be hydrophobic and oleophobic.

In some examples, the first hydrophobic/oleophobic material 18 may form a coating over the membrane 12. In other examples, the first hydrophobic/oleophobic material 18 may not form a coating over the membrane 12 but may instead be a surface treatment to the membrane 12. Surface treatment, in this situation, means that the first hydrophobic/oleophobic material 18 chemically reacts with the membrane 12 (such as the siliceous filler dispersed throughout the membrane 12) so as to form a hydrophobic/oleophobic region of the membrane 12.

The first hydrophobic/oleophobic material 18 may include at least one fluoro-alkyl group and/or include a polymer including at least one fluoro-alkyl group. The first hydrophobic/oleophobic material 18 may be a fluoro-alkyl group containing co-polymer. The first hydrophobic/oleophobic material 18 may be a polyacrylate co-polymer having a fluorinated polymer. In one non-limiting example, the first hydrophobic/oleophobic material 18 may include products sold under the Unidyne tradename, available from Daikin Industries, Ltd. (Osaka, Japan). The first hydrophobic/oleophobic material 18 may include any of the fluoro-alkyl group containing polymers or co-polymers described in U.S. Pat. No. 6,013,732 or 8,551,895, which are incorporated herein in their entireties by reference. The first hydrophobic/oleophobic material 18 may include a polymer including some fluorination in the side chains or ends of the polymer, with the backbone of the polymer being substantially free of fluorine groups (distinguishable from perfluorinated polymers).

The first hydrophobic/oleophobic material 18 may include an alkoxysilane compound having at least one fluoro-alkyl group. The first hydrophobic/oleophobic material 18 including the alkoxysilane compound having at least one fluoro-alkyl group may interact with the membrane 12 (such as with the siliceous filler) through a condensation reaction with filler and may form a hydrophobic/oleophobic region of the membrane 12. Non-limiting examples of the alkoxysilane compound having at least one fluoro-alkyl group are (tridecafluoro-1,1,2,2-tetrahydrooctyl)triethoxysilane (see Formula I below) or (tridecafluoro-1,1,2,2-tetrahydrooctyl)trimethoxysilane.

Formula I

As shown in FIG. 1, the first hydrophobic/oleophobic material 18 may be applied over the first side 14 of the membrane 12 without any material applied over the second side 16. Alternatively, the first hydrophobic/oleophobic material 18 may be applied over the first side 14 of the membrane 12 with material also being applied on the second side 16 (see FIGS. 2 and 3). Additional material may be applied over top of or underneath the first hydrophobic/oleophobic material 18. In some examples, the first hydrophobic/oleophobic material 18 is in direct contact with the first side 14 and/or the second side 16 of the membrane 12. The first hydrophobic/oleophobic material 18 may be applied to the first side 14 and/or the second side 16 of the membrane 12 using any suitable method such as spray application, curtain coating, dip coating, slot die coating, screen printing, and/or drawn-down coating, e.g., by means of a doctor blade or draw-down bar, techniques. In one non-limiting embodiment, the first hydrophobic/oleophobic material 18 is applied to the first side 14 of the membrane 12 using a draw-down method such that only the first side 14 of the membrane 12 is coated with first hydrophobic/oleophobic material 18 and not the second side 16.

B. Second Hydrophobic/Oleophobic Material

Referring to FIG. 3, the membrane may be coated with a second hydrophobic/oleophobic material 22. The a second hydrophobic/oleophobic material 22 may be applied to the first side 14 of the membrane 12 and/or the second side 16 of the membrane 12 (as shown in FIG. 3).

The second hydrophobic/oleophobic material 22 may be hydrophobic. The side (such as the first side 14 or the second side 16) of the membrane 12 over which the second hydrophobic/oleophobic material 22 is applied may demonstrate a water contact angle of at least 105°, such as at least 110°, at least 115°, at least 120°, at least 125°, at least 130°, at least 135°, at least 140°, or at least 150°.

The second hydrophobic/oleophobic material 22 may be chosen from any of the materials of the previously described first hydrophobic/oleophobic material 18.

As shown in FIG. 3, the second hydrophobic/oleophobic material 22 may be applied over the second side 16 of the membrane 12 opposite the first side 14, which has the first hydrophobic/oleophobic material 18 applied thereon. The second hydrophobic/oleophobic material 22 on the second side 16 may be the same hydrophobic/oleophobic material or a different hydrophobic/oleophobic material from the first hydrophobic/oleophobic material 18 on the first side 14. Additional materials may be applied over top of or underneath the second hydrophobic/oleophobic material 22. In some examples, the second hydrophobic/oleophobic material 22 is in direct contact with the first side 14 and/or the second side 16 of the membrane 12.

The second hydrophobic/oleophobic material 22 may be applied to the first side 14 and/or the second side 16 of the membrane 12 using any suitable method such as spray application, curtain coating, dip coating, slot die coating, screen printing, and/or drawn-down coating, e.g., by means of a doctor blade or draw-down bar, techniques. In one non-limiting embodiment, the second hydrophobic/oleophobic material 22 is applied to the second side 16 of the membrane 12 using a draw-down method such that only the second side 16 of the membrane 12 is coated with second hydrophobic/oleophobic material 22 and not the first side 14.

C. Hydrophilic Coating Layer

Referring to FIG. 2, the membrane 12 may be coated with at least one hydrophilic coating 20. The hydrophilic coating 20 may be applied to the first side 14 of the membrane and/or the second side 16 of the membrane 12 (as shown in FIG. 2).

The hydrophilic coating 20 may be hydrophilic. Hydrophilic means that the side of the membrane 12 over which the hydrophilic coating 20 is applied demonstrates a water contact angle of less than 90° using the Kruss Drop Shape Analysis. The side of the membrane 12 over which the hydrophilic coating 20 is applied may demonstrate a water contact angle of less than 85°, such as less than 80°, less than 70°, less than 60°, less than 50°, less than 40°, less than 30°, less than 20°, or less than 10°.

In some non-limiting embodiments, the hydrophilic coating 20 may include one or more of a polyoxazoline, triblock copolymers based on poly(ethylene glycol)-poly(propylene glycol)-poly(ethylene glycol), polyamide, oxidized polyethylene or its derivatives, polyethyleneoxide, polyvinylpyrrolidone, poly(meth)acrylic acid, polyethylene glycol or its derivatives, polypropylene oxide or its derivatives, a copolymer of poly(ethylene glycol) and polyethyleneoxide, polyvinyl alcohol, cellulose or its derivatives, collagen, polypeptides, guar, pectin, polyimide, poly(meth)acrylamide, polysaccharides, zwitterionic polymers, polyampholytes, and polyethylenimine As shown in FIG. 2, the hydrophilic coating 20 may be applied over the second side 16 of the membrane 12 opposite the first side 14, which has the first hydrophobic/oleophobic material 18 applied thereover. Additional materials may be applied over top of or underneath the hydrophilic coating 20. In some examples, the hydrophilic coating 20 is in direct contact with the first side 14 and/or the second side 16 of the membrane 12.

The hydrophilic coating 20 may be applied to the first side 14 and/or the second side 16 of the membrane 12 using any suitable method such as spray application, curtain coating, dip coating, slot die coating, screen printing, and/or drawn-down coating, e.g., by means of a doctor blade or draw-down bar, techniques. In some examples, the hydrophilic coating 20 is applied to the second side 16 of the membrane 12 using a draw-down method such that only the second side 16 of the membrane 12 is coated with hydrophilic coating 20 and not the first side 14.

In some examples, the membrane 12 may be pre-treated (before any other material is applied to the membrane 12, such as the first hydrophobic/oleophobic material 18, the second hydrophobic/oleophobic material 22, or other hydrophilic coating 20). The pre-treatment may be applied as a coating to the membrane 12, and the pre-treatment may be a hydrophilic coating, as previously described. The pre-treatment may improve uniformity of the subsequently applied material(s), such as the hydrophobic/oleophobic materials or other hydrophilic coating(s).

The hydrophilic pre-treatment may be applied to the membrane 12 using any suitable method. In one example, the membrane 12 is dipped into a bath including the hydrophilic pre-treatment. The hydrophilic pre-treatment may be applied using other art-related methods, such as spray application, curtain coating, slot die coating, screen printing, and/or drawn-down coating, e.g., by means of a doctor blade or draw-down bar, techniques. The hydrophilic pre-treatment may be applied to the first side 14, the second side 16, or the entire membrane 12. After the hydrophilic pre-treatment is applied, the pre-treated membrane 12 may be dried prior to any application of subsequent materials.

Volatile Material

The membrane 12 may allow a volatile material to travel therethrough. The volatile material may be in a reservoir on the first side 14 of the membrane 12 such that the first side 14 is a volatile material contact surface 14. The second side 16 may be a vapor release surface 16 not in contact with the volatile material in the reservoir but is the side from which the volatile material is released to the environment in a gaseous or vapor form.

Volatile material may be any material that is capable of conversion to a gaseous or vapor form, i.e., capable of vaporizing, at ambient room temperature and pressure, and in the absence of imparted additional or supplementary energy, e.g., in the form of heat and/or agitation. The volatile material may comprise an organic volatile material, which may include those volatile materials comprising a solvent-based material, or those which are dispersed in a solvent-based material. The volatile material may be in a liquid form and/or in a solid form, and may be naturally occurring or synthetically formed. When in a solid form, the volatile material may sublime from the solid form to the vapor form without passing thru an intermediate liquid form. The volatile material may optionally be combined or formulated with nonvolatile materials, such as a carrier, e.g., water and/or nonvolatile solvents. In the case of a solid volatile material, the nonvolatile carrier may be in the form of a porous material, e.g., a porous inorganic material, in which the solid volatile material is held. Also, the solid volatile material may be in the form of a semi-solid gel.

The volatile material may be a fragrance material, such as a naturally occurring or synthetic perfume oil. Examples of perfume oils from which the liquid volatile material may be selected include, but are not limited to, oil of bergamot, bitter orange, lemon, mandarin, caraway, cedar leaf, clove leaf, cedar wood, geranium, lavender, orange, origanum, petitgrain, white cedar, patchouli, neroili, rose absolute, and combinations thereof. Examples of solid fragrance materials from which the volatile material may be selected include, but are not limited to, vanillin, ethyl vanillin, coumarin, tonalid, calone, heliotropene, musk xylol, cedrol, musk ketone benzophenone, raspberry ketone, methyl naphthyl ketone beta, phenyl ethyl salicylate, veltol, maltol, maple lactone, proeugenol acetate, evemyl, and combinations thereof.

When volatile material is transferred from the volatile material contact surface 14 to the vapor release surface 16 of the membrane 12, it is believed that the volatile material is in a form selected from liquid, vapor and a combination thereof. In addition, it is believed that the volatile material, at least in part, moves through the network of interconnecting pores that communicate substantially throughout the membrane 12. The transfer of volatile material may occur at temperatures of from 15° C. to 40° C., e.g., from 15 or 18° C. to 30 or 35° C. and at ambient atmospheric pressure.

The volatile material transfer rate of the membrane 12 may be determined in accordance with the following description. A test reservoir, having an interior volume sufficient to contain 2 milliliters of a model volatile material, such as benzyl acetate, dipropyleneglycol, methyl ether acetate, limonene, or other similar material (benzyl acetate will be used herein), was fabricated from a clear thermoplastic polymer. The interior dimensions of the reservoir was defined by a circular diameter at the edge of the open face of approximately 4 centimeters and a depth of no greater than 1 centimeter. The open face was used to determine the volatile material transfer rate. With the test reservoir lying flat (with the open face facing upward), about 2 milliliters of benzyl acetate was introduced into the test reservoir. With benzyl acetate introduced into the test reservoir, a sheet of microporous material having a thickness of from 6 to 18 mils was placed over the open face/side of the test reservoir, such that 12.5 cm$^2$ of the volatile material contact surface of the microporous sheet was exposed to the interior of the reservoir. The test reservoir was weighed to obtain an initial weight of the entire charged assembly.

The volatile material transfer rate may be measured using non-restricted flow conditions. For the non-restricted flow conditions, the test reservoir, containing benzyl acetate and enclosed with the sheet of microporous material, was then placed, standing upright, in a laboratory chemical fume hood having approximate dimensions of 5 feet [1.52 meters] (height)×5 feet [1.52 meters](width)×2 feet [0.61 meters] (depth). With the test reservoir standing upright, benzyl acetate was in direct contact with at least a portion of the volatile material contact surface of the microporous sheet. The glass doors of the fume hood were pulled down, and the air flow through the hood was adjusted so as to have eight (8) turns (or turnovers) of hood volume per hour. Unless otherwise indicated, the temperature in the hood was maintained at 25° C.±5° C. The humidity within in the fume hood was ambient. The test reservoirs were regularly weighed in the hood. The calculated weight loss of benzyl acetate, in combination with the elapsed time and surface area of the microporous sheet exposed to the interior of the test reservoir, were used to determine the volatile transfer rate of the microporous sheet, in units of mg/(hour*cm$^2$).

The volatile material transfer rate may be measured using restricted flow conditions. For the restricted flow conditions the test reservoir containing benzyl acetate and enclosed with the sheet of microporous material, was then placed in a HDPE enclosed box, having approximate dimensions of 11 inches [0.28 meters] (height)×19 inches [0.48 meters] (width)×11 inches [0.28 meters] (depth). Enclosing the container was an 11 inch [0.28 meters]×19 inch [0.48 meters] cardboard sheet, wrapped with duct tape. The calculated weight loss of benzyl acetate, in combination with the elapsed time and surface area of the microporous sheet exposed to the interior of the test reservoir, were used to determine the volatile transfer rate of the microporous sheet, in units of mg/(hour*cm$^2$).

The volatile material transfer rate of the membrane 12 (using benzyl acetate as the model volatile material) according to the present invention under non-restricted flow conditions may be less than or equal to 0.7 mg/(hour*cm$^2$), or less than or equal to 0.6 mg/(hour*cm$^2$), or less than or equal to 0.55 mg/(hour*cm$^2$), or less than or equal to 0.50 mg/(hour*cm$^2$). The volatile material transfer rate of the membrane 12 may be equal to or greater than 0.02 mg/(hour*cm$^2$), or equal to or greater than 0.04 mg/(hour*cm$^2$), or equal to or greater than 0.30 mg/(hour*cm$^2$), or equal to or greater than 0.35 mg/(hour*cm$^2$). The volatile material transfer rate of the membrane 12 may range between any combination of these upper and lower values. For example, the volatile material transfer rate of the membrane 12 may be from 0.04 to 0.6 mg/(hour*cm$^2$), or from 0.2 to 0.6 mg/(hour*cm$^2$), or from 0.30 to 0.55 mg/(hour*cm$^2$), in each case inclusive of the recited values.

The volatile material transfer rate of the membrane 12 (using benzyl acetate as the model volatile material) according to the present invention under restricted flow conditions may be less than or equal to 0.1 mg/(hour*cm$^2$), or less than or equal to 0.08 mg/(hour*cm$^2$), or less than or equal to 0.06 mg/(hour*cm$^2$), or less than or equal to 0.05 mg/(hour*cm$^2$). The volatile material transfer rate of the membrane 12 may be equal to or greater than 0.02 mg/(hour*cm$^2$), or equal to or greater than 0.03 mg/(hour*cm$^2$), or equal to or greater than 0.04 mg/(hour*cm$^2$), or equal to or greater than 0.05 mg/(hour*cm$^2$). The volatile material transfer rate of the membrane may range between any combination of these upper and lower values. For example, the volatile material transfer rate of the membrane 12 may be from 0.02 to 0.1 mg/(hour*cm$^2$), or from 0.03 to 0.08 mg/(hour*cm$^2$), or from 0.04 to 0.06 mg/(hour*cm$^2$), in each case inclusive of the recited values.

The vapor release surface 16 may be substantially free of volatile material in liquid form. This is determined by the following procedure (e.g., using a sweat rating). Every 24 hours for at least 14 days, the exterior membrane surface on each assembly was visually inspected for liquid accumulation. The sweat rating used a numbering system, with "0" being no liquid accumulation; "1" being liquid accumulation on the substrate alone; "2" having liquid accumulation on the substrate and the ring gasket of the holder; and "3" having liquid accumulation on the substrate, seal and bottom metal lip of the holder. The average of all evaluations over time was used to determine the average sweat rating.

Applications of the Treated Microporous Membrane

The treated membranes 10 shown in FIGS. 1-3 may be configured for use in a fragrance delivery device. The fragrance delivery device may include an odorous volatile material (as previously described) contained in a reservoir. The volatile material contact surface 14 of the treated membrane 10 (having the first hydrophobic/oleophobic material 18) may be in contact with the volatile material in liquid or solid form. The vapor release surface 16 of the treated membrane may not be coated (FIG. 1), may have the hydrophilic coating 20 (FIG. 2), or may have the second hydrophobic/oleophobic material 22 (FIG. 3). It will be appreciated that in other embodiments (not shown in FIGS. 1-3), the volatile material contact surface 14 of the treated membrane 10 may be untreated, have the hydrophilic coating 20, or have the hydrophobic/oleophobic material 18 while the vapor release surface 16 has the hydrophobic/oleophobic material 18. In this way, one side of the treated membrane 10 (the volatile material contact surface 14 or the vapor release surface 16) may have the hydrophobic/oleophobic material 18, while the other of the volatile material contact surface 14 and the vapor release surface 16 is optionally untreated, has the hydrophilic coating 20, or has the hydrophobic/oleophobic material 18.

The fragrance delivery device may include a removable cap layer having a first and second surface. An adhesive layer may be interposed between the vapor release surface 16 of the membrane 12 and the second surface of the cap layer, such that the membrane 12 and volatile material are beneath the cap layer. The removable cap may be a peel seal which, optionally, includes a tab in order to facilitate removal from the membrane 12, thereby exposing the membrane 12 to activate the evaporative delivery of the volatile material. The cap layer may include at least one layer selected from the group consisting of metal foils, polymeric films, and combinations thereof. For example, the cap layer may include at least one polymeric film which has been printed or coated to appear metallized or "foil-like". Any know metal foils may be used, provided desired properties are achieved. Suitable polymeric films may include, but are not limited to, polyethylene film, polypropylene film, poly(ethylene terephthalate) film, polyester film, polyurethane film, poly(ester/urethane) film, or poly(vinyl alcohol) films. Any suitable polymeric film may be used, provided the desired properties are achieved. The cap layer also may include a metallized polymeric film either alone or in combination with a metal foil layer, a polymeric film layer, or both. The cap layer may include one layer or more than one layer in any combination.

The adhesive layer may include any of the known adhesives provided that the adhesive provides sufficient tack to keep the device sealed until activation by the consumer, while maintaining the removability of the cap layer. In a particular embodiment, the adhesive layer may include a pressure-sensitive adhesive ("PSA"), such as any of the PSA materials known in the art. Suitable PSA materials may include rubber-based adhesives, block co-polymer adhesives, polyisobutene-based adhesives, acrylic-based adhesives, silicone-based adhesives, polyurethane-based adhesives, vinyl-based adhesives, and mixtures thereof.

The treated membrane 10 of the fragrance delivery device may be configured to release odorous vapor from the vapor release side 16 of the treated membrane as the volatile material on the volatile material contact surface 14 penetrates through the treated membrane 10. The vapor release side 16 may be substantially free of volatile liquid. The treated membrane 12 may have a volatile material transfer rate within the range previously recited to as to release the odorous vapor at the desired rate.

The treated membrane 10 may also be configured for use in liquid-liquid or solid-liquid separation. In one example, the treated membrane 10 may be used for oil-water separation. In other examples, the treated membrane 10 may be used in membrane distillation or gas venting.

Method of Preparing Treated Microporous Membrane

The treated membrane 10 as previously described may be prepared using any suitable method.

According to one non-limiting embodiment, the treated membrane 10 may be prepared by providing the membrane 12 having the first side 14 and the second side 16. The membrane 12 may be made of the previously described thermoplastic organic polymer including a polyolefin. The membrane 12 may define a network of interconnecting pores communicating substantially throughout the membrane 12. The membrane 12 may include the previously described particulate filler distributed throughout the membrane 12.

The membrane 12 may optionally be pre-treated, such as using the previously described hydrophilic composition. The pre-treatment may be applied using any method, and, in one embodiment, the membrane 12 is dipped in the pre-treatment. The pre-treated membrane 12 may be dried after the pre-treatment is applied and prior to applying any further materials.

The first hydrophobic/oleophobic material 18 may be applied to at least a portion of the first side 14 and/or the second side 16 of the membrane 12 (pre-treated or not). The first hydrophobic/oleophobic material 18 may be applied using any method, and in one embodiment is applied to only the first side 14 using a drawdown method. In another example, the first hydrophobic/oleophobic material 18 may be applied by dipping the membrane 12 in the first hydrophobic/oleophobic material 18.

The hydrophilic coating 20 may be applied to at least a portion of the first side 14 and/or the second side 16 of the membrane 12 (pre-treated or not). The hydrophilic coating 20 may be applied using any method, and in one example is applied to only the second side 16 using a drawdown method.

The second hydrophobic/oleophobic material 22 may be applied to at least a portion of the first side 14 and/or the second side 16 of the membrane 12 (pre-treated or not). The second hydrophobic/oleophobic material 22 may be applied using any method, and in one example is applied to only the second side 14 using a drawdown method. In another example, the second hydrophobic/oleophobic material 22 may be applied by dipping the membrane 12 in the second hydrophobic/oleophobic material 22. The first hydrophobic/oleophobic material 18 may be the same or different from the second hydrophobic/oleophobic material 22.

The following examples are presented to exhibit the general principles of the invention. The invention should not be considered as limited to the specific examples presented. All parts and percentages in the examples are by weight unless otherwise indicated.

EXAMPLES 1-3

Preparation of Filled Microporous Membranes

Compositions of filled microporous membranes are shown in Table 2 below.

TABLE 2

| Ingredients (wt. %) | Example 1 | Example 2 | Example 3 |
|---|---|---|---|
| GUR ® 4170[1] | 9.08 | — | — |
| GUR ® 4130[2] | — | 9.16 | 9.60 |
| FINA ® 1288[3] | — | 9.16 | 8.75 |
| HI-SIL ® 135[4] | 31.77 | 30.89 | 24.86 |
| TIPURE ® R-103[5] | 1.40 | 1.28 | 1.71 |
| $CaCO_3$ | — | — | 10.03 |
| Calcium stearate | 0.41 | 0.26 | 0.27 |
| CYANOX ® 1790[6] | 0.33 | 0.26 | 0.18 |
| TUFFLO ® 6056[7] | 57.01 | 49.00 | 44.59 |

[1]An Ultra High Molecular Weight Polyethylene (UHMWPE), available from Celanese Corporation (Irving, TX)
[2]An Ultra High Molecular Weight Polyethylene (UHMWPE), available from Celanese Corporation (Irving, TX)
[3]High Density Polyethylene (HDPE), available from Total Petrochemicals USA Inc. (Houston, TX)
[4]Precipitated silica available from PPG Industries, Inc. (Pittsburgh, PA)
[5]Rutile titanium dioxide available from The Chemours Company (Wilmington, DE)
[6]A phenolic antioxidant available from Cytec Solvay Group (Woodland Park, NJ)
[7]A process oil available from PPC Lubricants (Jonestown, PA)

Step 1. Mix Preparation

The dry ingredients specified in Table 2 were weighed into a FM-130D Littleford plough blade mixer with one high intensity chopper style mixing blade. The dry ingredients were premixed for 15 seconds using the plough blades only. The process oil was then pumped in over 45-60 seconds via a hand pump through a spray nozzle at the top of the mixer, with only the plough blades running. The high intensity chopper blade was turned on, along with the plough blades, and the mix was mixed for 30 seconds, the mixer was shut off and the internal sides of the mixer were scraped down to ensure all ingredients were evenly mixed. The mixer was turned back on with both high intensity chopper and plough blades turned on, and the mix was mixed for an additional 30 seconds. The resultant mixtures were extruded as described in Step 2.

Step 2. Extrusion, Calendering and Extraction

The mixes of the Examples 1-3 were extruded and calendered into the final sheet form using an extrusion system including a feeding, extrusion and calendering system described as follows. A gravimetric loss in weight feed system (K-iron model #K2MLT35D5) was used to feed each of the respective mixes into a 27 mm twin screw extruder (model # was Leistritz Micro-27gg). The extruder barrel was comprised of eight temperature zones and a heated adaptor to the sheet die. The extrusion mixture feed port was located just prior to the first temperature zone. An atmospheric vent was located in the third temperature zone. A vacuum vent was located in the seventh temperature zone.

The mix was fed into the extruder at a rate of 90 g/minute. Additional processing oil also was injected at the first temperature zone, as required, to achieve the desired total oil content in the extruded sheet. The oil contained in the extruded sheet (extrudate) being discharged from the extruder is referenced herein as the "extrudate oil weight percent".

Extrudate from the barrel was discharged into a 15-centimeter wide sheet Masterflex® die having a 1.5 millimeter discharge opening. The extrusion melt temperature was 203-210° C. and the throughput was 7.5 kilograms per hour.

The calendering process was accomplished using a three-roll vertical calender stack with one nip point and one cooling roll. Each of the rolls had a chrome surface. Roll dimensions were approximately 41 cm in length and 14 cm in diameter. The top roll temperature was maintained between 135° C. to 140° C. The middle roll temperature was maintained between 140° C. to 145° C. The bottom roll was a cooling roll wherein the temperature was maintained between 10-21° C. The extrudate was calendered into sheet form and passed over the bottom water cooled roll and wound up.

A sample of sheet cut to a width up to 25.4 cm and length of 305 cm was rolled up and placed in a canister and exposed to hot liquid 1,1,2-trichloroethylene for approximately 7-8 hours to extract oil from the sheet sample. Afterwards, the extracted sheet was air dried and subjected to test methods described hereinafter.

EXAMPLES 4-7 AND COMPARATIVE EXAMPLES 8-13

Preparation of Coated Microporous Membranes

Step 1. Preparation of Coating Solutions

Hydrophilic Coating Composition 2A:

Poly (2-ethyl-2-oxazoline), (20 g, weight average molecular weight (Mw)~50,000) was dispersed in cool water (910 g) under mild agitation in a 4000 mL beaker. The mixture was stirred for 4 hours, followed by addition of PLURONIC®17R2 (10 g, a Block Copolymer Surfactant available from BASF (Ludwigshafen, Germany)) and 2-butoxyethanol (60 g), after which the resultant solution was stirred for an additional 30 minutes.

Hydrophilic Coating Composition 2B:

SELVOL® 325 (4 g, polyvinyl alcohol available from Sekisui Specialty Chemicals America (Dallas, Tex.)) was dispersed in cool water (96 g) under mild agitation in a 300 mL beaker using a 1 inch (2.54 cm) paddle stirrer driven by an electric stir motor. The mixture was heated to 190° F. (87.8° C.) and stirred for approximately 25 minutes until completely dissolved. The resultant solution was cooled to room temperature with stirring.

Hydrophobic/Oleophobic Coating Composition 2C:

UNIDYNE® 8112 (15 g, available from Daikin America, Inc. (Orangeburg, N.Y.)) was dispersed in cool water (85 g) under mild agitation in a 400 mL beaker.

Step 2. Coating Procedures

All membranes were cut to 8.5×11-inch [0.22×0.28 m] sheets prior to treatment with any coating composition. Examples 4-7 comprise hydrophobic/oleophobic composition 2C. Examples 5-7 were first treated with hydrophilic composition 2A prior to application of the hydrophobic/oleophobic composition 2C. Examples 4-6 were coated on only one side with the hydrophobic/oleophobic composition 2C, while Example 7 was coated on both sides.

For Examples 5-7, hydrophilic composition 2A was applied directly to the membrane prepared in Part 1 as indicated in Table 3. The 8.5×11-inch [0.22×0.28 m] sheet was immersed into composition 2A for a period of five minutes, after which the sheet was removed, and excess solution was allowed to drip off. The coated microporous material was then clamped on an aluminum frame which was fitted with a gasket to prevent the film from shrinking during drying. The framed membrane was then dried in an oven at 95° C. for 15 minutes.

Example 4, as well as the membranes of Examples 5-7 treated above, were then treated with the hydrophobic/oleophobic composition 2C. For Example 4, the membrane indicated in Table 3 was coated without prior treatment. For Examples 5-7, the hydrophobic/oleophobic composition was applied to the previously treated membranes described above. In each case, the 8.5×11-inch [0.22×0.28 m] sheet was placed on a clean glass surface and taped along the short side Composition 2C was applied directly to the microporous substrate or, where indicated, the microporous substrate treated with composition 2A. Each substrate had been tared on a balance prior to placing the sheet, Side A facing up, on a clean glass surface and using tape to adhere the top corners of the sheet to the glass. A piece of clear 10 mil thick polyester 11 inch (0.28 m)×3 inch (0.08 m) was positioned to overlap across the top edge of the sheet and affixed to the glass surface with tape. A wire wrapped metering rod #3 from Diversified Enterprises was placed on the polyester near the top edge. A 10 to 20 mL quantity of coating was deposited as a bead strip (approximately ¼ inch (0.64 cm) wide) directly next to and touching the metering rod using a disposable pipette.

The bar was drawn down across the sheet at approximately a constant rate. The resultant wet sheet was removed from the glass surface, immediately placed on the previously tared balance, weighed, then placed in a forced air oven and dried at 95° C. for 2 minutes. The dried sheet was removed from oven and the same coating procedure was repeated on Side B only for Example 5.

The Comparative Examples were left uncoated, or coated with hydrophilic coatings only. Comparative Example 11 and Comparative Example 12 were both treated with Composition 2A as described above. Comparative Example 12 was coated on Side A with an additional hydrophilic solution, 2B, which was applied in the same manner as described for composition 2C above. Comparative Example 13 was provided, which was a PVDF membrane fused with a super hydrophobic composition. This material is commercially available as DURAPEL® GVSP, available from MilliporeSigma (Billerica, Mass.).

Part 3. Physical Properties Testing of Membranes

Each of the membranes, treated membranes, and comparative untreated membranes were characterized by testing the physical properties described below.

Gurley Porosity:

This test was performed on dry membrane samples. Porosity was determined using a Gurley Precision Densometer, model 4340, manufactured by GPI Gurley Precision Instruments (Troy, N.Y.). The Porosity reported was a measure of the rate of air flow through a sample or it's resistance to an air flow through the sample. The unit of measure is a "Gurley second" and represents the time in seconds to pass 100 cc of air through a 1 inch square area using a pressure differential of 4.88 inches of water. Lower values equate to less air flow resistance (more air is allowed to pass freely, e.g., more porous). The measurements were completed using the procedure listed in the manual, MODEL 4340 Automatic Densometer and Smoothness Tester Instruction Manual. TAPPI method T 460 om-06-Air Resistance of Paper can also be referenced for the basic principles of the measurement.

Density:

The density of the above-described examples was determined by dividing the average weight of two specimens measuring 4.5×5 inches (11.43 cm×12.7 cm) that were cut from each sample by the average volume of those specimens.

Pore Size:

The volume average diameter of the pores of the microporous material was determined by mercury porosimetry using an Autoscan mercury porosimeter (Quantachrome Instruments (Boynton Beach, Fla.)) in accordance with the operating manual accompanying the instrument. The volume average pore radius for a single scan was determined automatically by the porosimeter. In operating the porosimeter, a scan was made in the high pressure range (from 138 kilopascals absolute to 227 megapascals absolute). If 2 percent or less of the total intruded volume occurred at the low end (from 138 to 250 kilopascals absolute) of the high pressure range, the volume average pore diameter was taken as twice the volume average pore radius determined by the porosimeter. Otherwise, an additional scan was made in the low pressure range (from 7 to 165 kilopascals absolute) and the volume average pore diameter was calculated according to the equation:

$$d = 2[v_1 r_1/w_1 + v_2 r_2/w_2]/[v_1/w_1 + v_2/w_2]$$

where, d is the volume average pore diameter; $v_1$ is the total volume of mercury intruded in the high pressure range; $v_2$ is the total volume of mercury intruded in the low pressure range; $r_1$ is the volume average pore radius determined from the high pressure scan; $r_2$ is the volume average pore radius determined from the low pressure scan; $w_1$ is the weight of the sample subjected to the high pressure scan; and $w_2$ is the weight of the sample subjected to the low pressure scan.

Contact angle: was measured on a VCA 2500XE video contact angle system, available from AST Products, Inc. (Billerica, Mass.) using 1 microliter of ultrapure water. On all samples, contact angle was measured on Side A.

Oil rating: was measured with AATCC test method 118-2007. In cases where Sides A and B were different, the oil rating was measured on Side A.

TABLE 3

| Example | Substrate | Side A | Side B | Porosity, Gurley (sec) | Density, (g/cm$^2$) | Mean pore size (microns) | Contact Angle (Side A) | Oil Rating (Side A) |
|---|---|---|---|---|---|---|---|---|
| 4 | Example 3 | 2C | — | 8477 | 0.9 | 0.03 | 107 | 7 |
| 5 | Example 1 | 2A/2C | 2A | 1297 | 0.57 | 0.05 | 118 | 7 |
| 6 | Example 3 | 2A/2C | 2A | 8477 | 0.9 | 0.03 | 107 | 7 |
| 7 | Example 3 | 2A/2C | 2A/2C | 3096 | 0.74 | 0.04 | 115 | 7 |
| CE-8 | Example 1 | — | — | 1297 | 0.55 | 0.05 | 114 | 2 |
| CE-9 | Example 2 | — | — | 5959 | 0.66 | 0.04 | 116 | 2 |
| CE-10 | Example 3 | — | — | 8477 | 0.74 | 0.03 | 105 | 2 |
| CE-11 | Example 2 | 2A | 2A | 5959 | 0.66 | 0.05 | <20 | 2 |
| CE-12 | Example 1 | 2A/2B | 2A | 1297 | 0.56 | 0.05 | 51 | 3 |
| CE-13 | DURAPEL® GVSP[8] | — | — | 150 | 0.67 | 0.44[9] | 153 | 6 |

[8]A PVDF porous membrane with a superhydrophobic surface, available from MilliporeSigma (Billerica, MA).

[9]Durapel GVSP has a reported mean pore size of 0.22 micron. Data in Table 3 is as measured according to the procedures described above.

Part 4. Volatile Material Transfer Rate and Sweat Rating Tests

Part 4A: Assembly of Testing Apparatus

The holder assembly used for evaporation rate and performance testing of a membrane consisted of a front clamp with a ring gasket, a back clamp, test reservoir cup, and four screws. The test reservoir cup was fabricated from a clear thermoplastic polymer, having interior dimensions defined by a circular diameter at the edge of the open face of approximately 4 centimeters and a depth of no greater than 1 centimeter. The open face was used to determine the volatile material transfer rate.

Each clamp of the holder assembly had a 1.5 inch (3.8 cm) diameter circular opening to accommodate the test reservoir cup and provide an opening to expose the membrane under test. When placing a membrane under test, the back clamp of the holder assembly was placed on top of a cork ring. The test reservoir cup was placed in the back clamp and charged with an amount of benzyl acetate as described below, used to simulate fragrance compositions. In Table 4, where "full" testing is indicated, 2 mL benzyl acetate was placed in the reservoir. "Quarter" testing indicated the placement of 0.5 mL benzyl acetate in the reservoir. An approximately 2 inch (5.1 cm) diameter disk was cut out of the membrane sheet and placed directly over and in contact with the edge of the reservoir cup such that 12.5 cm$^2$ of the surface (side of interest) of the microporous sheet was exposed to the interior of the reservoir. When a coated microporous sheet was used, the membrane was oriented such that Side A was exposed to the interior of the reservoir, with the exception of Example 5B, where the Side B was exposed to the interior of the reservoir.

The front clamp of the holder was carefully placed over the entire assembly, with the screw holes aligned and so as not to disturb the membrane disk. The screws were attached and tightened enough to prevent leaking. The ring gasket created a seal. Five replicates were assembled for each membrane tested.

Part 4B: Volatile Material Transfer Rate Test

Each holder assembly was weighed to obtain an initial weight of the entire charged assembly. The assembly was then placed upright such that the membrane was oriented vertically and benzyl acetate was in direct contact with at least a portion of the test membrane. The upright (vertically oriented) assembly was placed in an environment defined below according to the airflow, maintained at 25°±5° C. The humidity within in environment was ambient. The test reservoirs were weighed every 24 hours for a minimum of 14 days. The calculated weight loss of benzyl acetate over the entire time period, in combination with the elapsed time and surface area of the microporous sheet exposed to the interior of the test reservoir, were used to determine the volatile material transfer rate of the microporous sheet, in units of mg/(hour*cm$^2$). The average evaporation rate (mg/hr) of the replicates was determined for the entire assembly in Table 4. The average evaporation rate was converted to volatile material transfer rate according to the following formula:

$$\text{Average Evaporation Rate (mg/hr)}/12.5 \text{ cm}^2 = \text{Volatile Material Transfer Rate (mg/(hour*cm}^2\text{))}$$

The reported values in Table 4 are the average of all five samples over the entire testing period.

Air Flow Conditions

Examples tested under "non-restricted" conditions were placed laboratory chemical fume hood having approximate dimensions of 5 feet (1.52 m) (height)×5 (1.52 m) feet (width)×2 (0.61 m) feet (depth). The glass doors of the fume hood were pulled down, and the air flow through the hood was adjusted so as to have eight (8) turns (or turnovers) of hood volume per hour.

Examples tested under "restricted" conditions were placed in a HDPE enclosed box, having approximate dimensions of 11 inches (0.28 m) (height)×19 inches (0.48 m) (width)×11 inches (0.28 m) (depth). Enclosing the container was an 11×19 inch (0.28×0.48 m) cardboard sheet, wrapped with duct tape.

Part 4C: Sweat Rating

Concurrent with the volatile material transfer rate testing, every 24 hours for at least 14 days, the exterior membrane surface on each assembly was visually inspected for liquid accumulation. The sweat rating used a numbering system, with "0" being no liquid accumulation; "1" being liquid accumulation on the substrate alone; "2" having liquid accumulation on the substrate and the ring gasket of the holder; and "3" having liquid accumulation on the substrate, seal and bottom metal lip of the holder. The average of all evaluations over time for all five replicates were used to determine the average sweat rating reported below in Table 4.

TABLE 4

| | Volatile Material Transfer Rate (mg/(hr * cm$^2$)) | | | | Sweat Rating | |
|---|---|---|---|---|---|---|
| Example | Full Non-restricted | Full Restricted | Quarter Charge Non-restricted | Quarter Charge Restricted | Full Non-restricted | Full Restricted |
| 4 | 0.33 | 0.06 | 0.27 | 0.05 | 0 | 0 |
| 5A | 0.28 | 0.04 | 0.18 | 0.04 | 0 | 0 |
| 5B | 0.29 | 0.05 | 0.20 | 0.03 | 0 | 0 |
| 6 | 0.33 | 0.05 | 0.27 | 0.05 | 0 | 0 |
| 7 | 0.18 | 0.06 | 0.25 | 0.03 | 0 | 0 |
| CE-8 | 0.3 | 0.12 | 0.17 | 0.04 | 2.15 | 2.4 |
| CE-9 | 0.31 | 0.03 | 0.19 | 0.04 | 0 | 0.8 |
| CE-10 | 0.29 | 0.04 | 0.3 | 0.04 | 0 | 0.47 |
| CE-11 | 0.38 | 0.07 | 0.3 | 0.06 | 0 | 0.3 |
| CE-12 | 0.25 | 0.04 | 0.17 | 0.03 | 0.14 | 0.25 |
| CE-13 | 0.1 | <<0.01[10] | 0.1 | <<0.01[10] | 0 | N/A[10] |

[10]Over a 14 day period, no measurable change in weight was observed under restricted conditions, indicating that the membrane was not operating as a vapor permeable membrane. Thus, a sweat rating was not relevant.

The present invention further includes the subject matter of the following clauses.

Clause 1: A treated vapor permeable microporous membrane comprising: a microporous membrane comprising a first side and a second side opposite the first side, the membrane comprising a thermoplastic organic polymer comprising a polyolefin, the membrane defining a network of interconnecting pores communicating substantially throughout the membrane; finely divided, substantially water-insoluble particulate filler distributed throughout the membrane and constituting 10 to 90 weight percent of the membrane, based on the total weight of the membrane and the particulate filler; and a first hydrophobic/oleophobic material over at least a portion of the first side, wherein the polyolefin comprises at least 2 weight percent of the membrane, based on the total weight of the membrane and the particulate filler, wherein the membrane has a mean pore size of up to 0.2 μm.

Clause 2: The treated membrane of clause 1, wherein the first hydrophobic/oleophobic material comprises at least one fluoro-alkyl group.

Clause 3: The treated membrane of clauses 1 or 2, wherein the first hydrophobic/oleophobic material comprises a fluoro-alkyl group containing co-polymer.

Clause 4: The treated membrane of any of clauses 1-3, wherein at least a portion of the first side demonstrates an oil rating of at least 6 based on AATCC test method 118-2007.

Clause 5: The treated membrane of any of clauses 1-4, wherein at least a portion of the first side demonstrates a water contact angle of at least 105°.

Clause 6: The treated membrane of any of clauses 1-5, wherein the particulate filler comprises siliceous particles comprising particulate silica.

Clause 7: The treated membrane of any of clauses 1-6, wherein the membrane has a density between 0.4 g/cm$^3$ and 1.0 g/cm$^3$.

Clause 8: The treated membrane of any of clauses 1-7, further comprising a second hydrophobic/oleophobic material over at least a portion of the second side.

Clause 9: The treated membrane of any of clauses 1-8, further comprising a hydrophilic coating over at least a portion of the second side.

Clause 10: The treated membrane of clause 9, wherein the hydrophilic coating comprises one or more of a polyoxazoline, triblock copolymers based on poly(ethylene glycol)-poly(propylene glycol)-poly(ethylene glycol), polyamide, oxidized polyethylene or its derivatives, polyethyleneoxide, polyvinylpyrrolidone, poly(meth)acrylic acid, polyethylene glycol or its derivatives, polypropylene oxide or its derivatives, a copolymer of poly(ethylene glycol) and polyethyleneoxide, polyvinyl alcohol, cellulose or its derivatives, collagen, polypeptides, guar, pectin, polyimide, poly(meth)acrylamide, polysaccharides, zwitterionic polymers, polyampholytes, and polyethylenimine Clause 11: The treated membrane of any of clauses 1-10, wherein the first side or the second side comprises a volatile material contact surface and the other of the first side and the second side comprises a vapor release surface, wherein the treated membrane is configured to release odorous vapor from the vapor release surface of a fragrance delivery device.

Clause 12: A method of preparing a treated vapor permeable microporous membrane comprising: providing a microporous membrane comprising a first side and a second side opposite the first side, the membrane comprising a thermoplastic organic polymer comprising a polyolefin, the membrane defining a network of interconnecting pores communicating substantially throughout the membrane, the membrane having finely divided, particulate filler distributed throughout the membrane; and applying a first hydrophobic/oleophobic material over at least a portion of the first side.

Clause 13: The method of clause 12, further comprising, prior to applying the first hydrophobic/oleophobic material over at least a portion of the first side, applying a first hydrophilic coating over at least a portion of the first side.

Clause 14: The method of clause 13, wherein the first hydrophilic coating comprises at least one of a polyoxazoline, triblock copolymers based on poly(ethylene glycol)-poly(propylene glycol)-poly(ethylene glycol), polyamide, oxidized polyethylene or its derivatives, polyethyleneoxide, polyvinylpyrrolidone, poly(meth)acrylic acid, polyethylene glycol or its derivatives, polypropylene oxide or its derivatives, a copolymer of poly(ethylene glycol) and polyethyleneoxide, polyvinyl alcohol, cellulose or its derivatives, collagen, polypeptides, guar, pectin, polyimide, poly(meth)acrylamide, polysaccharides, zwitterionic polymers, polyampholytes, and polyethylenimine Clause 15: The method of clause 13 or 14, further comprising, drying the membrane comprising the first hydrophilic coating prior to applying the first hydrophobic/oleophobicmaterial over at least a portion of the first side.

Clause 16: The method of any of clauses 12-15, wherein the first hydrophobic/oleophobic material is applied over the portion of the first side using a drawdown method.

Clause 17: The method of any of clauses 12-16, further comprising applying a second hydrophilic coating over at least a portion of the second side of the membrane.

Clause 18: The method of any of clauses 12-17, further comprising applying a second hydrophobic/oleophobic material over at least a portion of the second side of the membrane.

Clause 19: The method of any of clauses 12-18, wherein the first hydrophobic/oleophobic material comprises at least one fluoro-alkyl group.

Clause 20: The method of any of clauses 12-19, wherein the particulate filler comprises siliceous particles comprising particulate silica.

Clause 21: The treated membrane of any of clauses 1-11, wherein the first hydrophobic/oleophobic material comprises an alkoxysilane compound having at least one fluoro-alkyl group.

Clause 22: The method of any of clauses 12-20, wherein the first hydrophobic/oleophobic material comprises a fluoro-alkyl group containing co-polymer.

Clause 23: The method of any of clauses 12-20 or 22, wherein the first side demonstrates an oil rating of at least 6 based on AATCC test method 118-2007.

Clause 24: The method of any of clauses 12-20, 22, or 23, wherein the first side demonstrates a water contact angle of at least 105°.

Clause 25: The method of any of clauses 12-20 or 22-24, wherein the particulate filler constitutes from 10 to 90 weight percent of the membrane, based on the total weight of the membrane and the particulate filler.

Clause 26: The method of any of clauses 12-20 or 22-25, wherein the membrane has a density between 0.4 g/cm$^3$ and 1.0 g/cm$^3$.

Clause 27: The method of any of clauses 17-20 or 22-26, wherein the hydrophilic coating comprises one or more of a polyoxazoline, triblock copolymers based on poly(ethylene glycol)-poly(propylene glycol)-poly(ethylene glycol), polyethyleneimine, polyamide, oxidized polyethylene or its derivatives, polyethyleneoxide, polyethyleneglycol, polyvinylpyrrolidone, polyacrylic acid, polymethacrylic acid, polyethylene glycol derivatives, polypropylene oxide or its derivatives, a copolymer of poly(ethylene glycol) and polyethyleneoxide, polyvinyl alcohol, ethylene vinyl acetate, cellulose or its derivatives, collagen, polypeptides, guar, pectin, polyimide, polypeptide, poly(meth)acrylate, poly(meth)acrylamide, polysaccharides, zwitterionic polymers, polyampholytes, and polyethylenimine Clause 28: The method of any of clauses 12-20 or 22-27, wherein the first side comprises a volatile material contact surface and the second side comprises a vapor release surface, wherein the treated membrane is configured to release odorous vapor from the vapor release surface of a fragrance delivery device.

Clause 29: The treated membrane of any of clauses 6-11 or 21, wherein the particulate filler further comprises calcium carbonate.

Whereas particular embodiments of this invention have been described above for purposes of illustration, it will be evident to those skilled in the art that numerous variations of the details of the present invention may be made without departing from the invention as defined in the appended claims.

The invention claimed is:

1. A treated vapor permeable microporous membrane, comprising:
   a microporous membrane comprising a first side and a second side opposite the first side, the membrane comprising a thermoplastic organic polymer comprising a polyolefin, the membrane defining a network of interconnecting pores communicating substantially throughout the membrane;
   substantially water-insoluble particulate filler distributed throughout the membrane and constituting 10 to 90 weight percent of the membrane, based on the total weight of the membrane and the particulate filler, wherein at least 90 weight percent of the particulate filler has a particle size of from 0.5-200 micrometers;
   a first hydrophobic/oleophobic material over at least a portion of the first side, wherein the first hydrophobic/oleophobic material forms a continuous layer over at least a portion of the first side; and
   a hydrophilic coating over at least a portion of the second side,
   wherein the polyolefin comprises at least 2 weight percent of the membrane, based on the total weight of the membrane and the particulate filler,
   wherein the untreated microporous membrane has a volume average diameter of the pores ranging from 0.02 to 0.075 micrometers, wherein the treated vapor permeable microporous membrane has substantially the same volume average diameter of the pores compared to the untreated membrane and wherein the pores of the microporous membrane are not occluded by the first hydrophobic/oleophobic material and the hydrophilic coating,
   wherein the first hydrophobic/oleophobic material comprises a fluoro-alkyl group containing co-polymer.

2. The treated membrane of claim 1, wherein at least a portion of the first side demonstrates an oil rating of at least 6 based on AATCC test method 118-2007.

3. The treated membrane of claim 1, wherein at least a portion of the first side demonstrates a water contact angle of at least 105°.

4. The treated membrane of claim 1, wherein the particulate filler comprises siliceous particles comprising particulate silica.

5. The treated membrane of claim 4, wherein the particulate filler further comprises calcium carbonate.

6. The treated membrane of claim 1, wherein the membrane has a density between 0.4 g/cm$^3$ and 1.0 g/cm$^3$.

7. The treated membrane of claim 1, further comprising a second hydrophobic/oleophobic material over at least a portion of the hydrophilic coating.

8. The treated membrane of claim 1, wherein the hydrophilic coating comprises one or more of a polyoxazoline, triblock copolymers based on poly(ethylene glycol)-poly(propylene glycol)-poly(ethylene glycol), polyamide, oxidized polyethylene or its derivatives, polyethyleneoxide, polyvinylpyrrolidone, poly(meth)acrylic acid, polyethylene glycol or its derivatives, polypropylene oxide or its derivatives, a copolymer of poly(ethylene glycol) and polyethyleneoxide, polyvinyl alcohol, cellulose or its derivatives, collagen, polypeptides, guar, pectin, polyimide, poly(meth)acrylamide, polysaccharides, zwitterionic polymers, polyampholytes, and polyethylenimine.

9. The treated membrane of claim 1, wherein the first side or the second side comprises a volatile material contact surface and the other of the first side and the second side comprises a vapor release surface, wherein the treated membrane is configured to release odorous vapor from the vapor release surface of a fragrance delivery device and to contact a volatile material of the fragrance delivery device on the volatile material contact surface.

10. The treated membrane of claim 1, wherein the first hydrophobic/oleophobic material comprises an alkoxysilane compound having at least one fluoro-alkyl group.

11. The treated membrane of claim 1, wherein the treated vapor permeable microporous membrane has a volume average diameter of the pores ranging from 0.03 to 0.05 micrometers.

12. The treated membrane of claim 1, wherein the substantially the same volume average diameter of the pores comprise the volume average diameter of the pores of the treated membrane being within 0.01 micrometers of the volume average diameter of the pores of the untreated membrane.

13. The treated membrane of claim 1, comprising a hydrophilic coating over at least a portion of the first side, wherein at least a portion of the hydrophilic coating is interposed between the first side of the membrane and the first hydrophobic/oleophobic material.

14. The treated membrane of claim 1, comprising a second hydrophobic/oleophobic material over at least a portion of the hydrophilic coating.

15. A method of preparing a treated vapor permeable microporous membrane comprising:
   providing a microporous membrane comprising a first side and a second side opposite the first side, the membrane comprising a thermoplastic organic polymer comprising a polyolefin, the membrane defining a network of interconnecting pores communicating substantially throughout the membrane, the membrane having particulate filler distributed throughout the membrane, wherein at least 90 weight percent of the particulate filler has a particle size of from 0.5-200 micrometers, and wherein the untreated microporous membrane has a volume average diameter of the pores ranging from 0.02 to 0.075 micrometers;
   applying a first hydrophobic/oleophobic material over at least a portion of the first side to form a continuous layer over at least a portion of the first side; and
   applying a hydrophilic coating over at least a portion of the second side, wherein the treated vapor permeable microporous membrane has substantially the same volume average diameter of the pores compared to the untreated membrane and wherein the pores of the microporous membrane are not occluded by the first hydrophobic/oleophobic material and the hydrophilic coating, wherein the first hydrophobic/oleophobic material comprises a fluoro-alkyl group containing co-polymer.

16. The method of claim 15, further comprising, prior to applying the first hydrophobic/oleophobic material over at least a portion of the first side, applying a first hydrophilic coating over at least a portion of the first side.

17. The method of claim 16, wherein the first hydrophilic coating comprises at least one of a polyoxazoline, triblock copolymers based on poly(ethylene glycol)-poly(propylene glycol)-poly(ethylene glycol), polyamide, oxidized polyethylene or its derivatives, polyethyleneoxide, polyvinylpyrrolidone, poly(meth)acrylic acid, polyethylene glycol or its derivatives, polypropylene oxide or its derivatives, a copolymer of poly(ethylene glycol) and polyethyleneoxide, polyvinyl alcohol, cellulose or its derivatives, collagen, polypeptides, guar, pectin, polyimide, poly(meth)acrylamide, polysaccharides, zwitterionic polymers, polyampholytes, and polyethylenimine.

18. The method of claim 16, further comprising, drying the membrane comprising the first hydrophilic coating prior to applying the first hydrophobic/oleophobic material over at least a portion of the first side.

19. The method of claim 15, wherein the first hydrophobic/oleophobic material is applied over the portion of the first side using a drawdown method.

20. The method of claim 15, further comprising applying a second hydrophobic/oleophobic material over at least a portion of the hydrophilic coating on the second side of the membrane.

21. The method of claim 15, wherein the first hydrophobic/oleophobic material comprises at least one alkoxysilane compound having at least one fluoro-alkyl group.

22. The method of claim 15, wherein the particulate filler comprises siliceous particles comprising particulate silica.

* * * * *